(12) United States Patent
Stergiopulos

(10) Patent No.: US 6,974,445 B2
(45) Date of Patent: Dec. 13, 2005

(54) IMPLANTABLE MEDICAL DEVICE FOR DELIVERING A LIQUID

(75) Inventor: Nikolaus Stergiopulos, St-Sulpice (CH)

(73) Assignee: Endoart SA, (CH)

( * ) Notice: Subject to any disclaimer, the term of this patent is extended or adjusted under 35 U.S.C. 154(b) by 1 day.

(21) Appl. No.: 10/398,764

(22) PCT Filed: Oct. 19, 2001

(86) PCT No.: PCT/CH01/00624

§ 371 (c)(1),
(2), (4) Date: Apr. 10, 2003

(87) PCT Pub. No.: WO02/36184

PCT Pub. Date: May 10, 2002

(65) Prior Publication Data

US 2004/0044332 A1  Mar. 4, 2004

(30) Foreign Application Priority Data

Nov. 3, 2000  (CH) ..................................... 2146/00

(51) Int. Cl.[7] .......................... A61M 1/00; A61M 5/00; A61M 31/00; A61M 37/00
(52) U.S. Cl. .................. 604/288.03; 604/153; 604/246
(58) Field of Search ............ 604/93.01, 131, 604/132, 152, 153, 246, 248, 249, 288.01, 604/288.02, 288.03, 288.04, 890.1, 891.1, 604/892.1

(56) References Cited

U.S. PATENT DOCUMENTS

| 5,067,943 A | * | 11/1991 | Burke ......................... 604/141 |
| 5,193,990 A |   | 3/1993 | Lanigan et al. |
| 5,368,571 A | * | 11/1994 | Horres, Jr. ................... 604/131 |
| 5,785,681 A |   | 7/1998 | Indravudh |
| 6,554,822 B1 | * | 4/2003 | Holschneider et al. ... 604/892.1 |

FOREIGN PATENT DOCUMENTS

EP  0 387 439  9/1990

* cited by examiner

Primary Examiner—Nicholas D. Lucchesi
Assistant Examiner—Mark K. Han
(74) Attorney, Agent, or Firm—Nicola A. Pisano, Esq.; Luce, Forward, Hamilton & Scripps LLP

(57) ABSTRACT

The invention concerns an implantable device (1) for delivering medicines in liquid form comprising: a reservoir (2) provided with an inlet (3) and an outlet (10), said reservoir (2) being adapted to expel the liquid; a variable volume chamber (5) provided with an inlet (11) and an outlet (12), the volume of the variable volume chamber (5) being in particular smaller than that of the reservoir (2); a first conduit (6) communicating the outlet (10) of the reservoir (2) with the inlet (11) of the variable volume chamber (5) to fill the latter; a second conduit (8) whereof one of the ends is connected on the outlet (12) of the variable volume chamber (5).

20 Claims, 2 Drawing Sheets

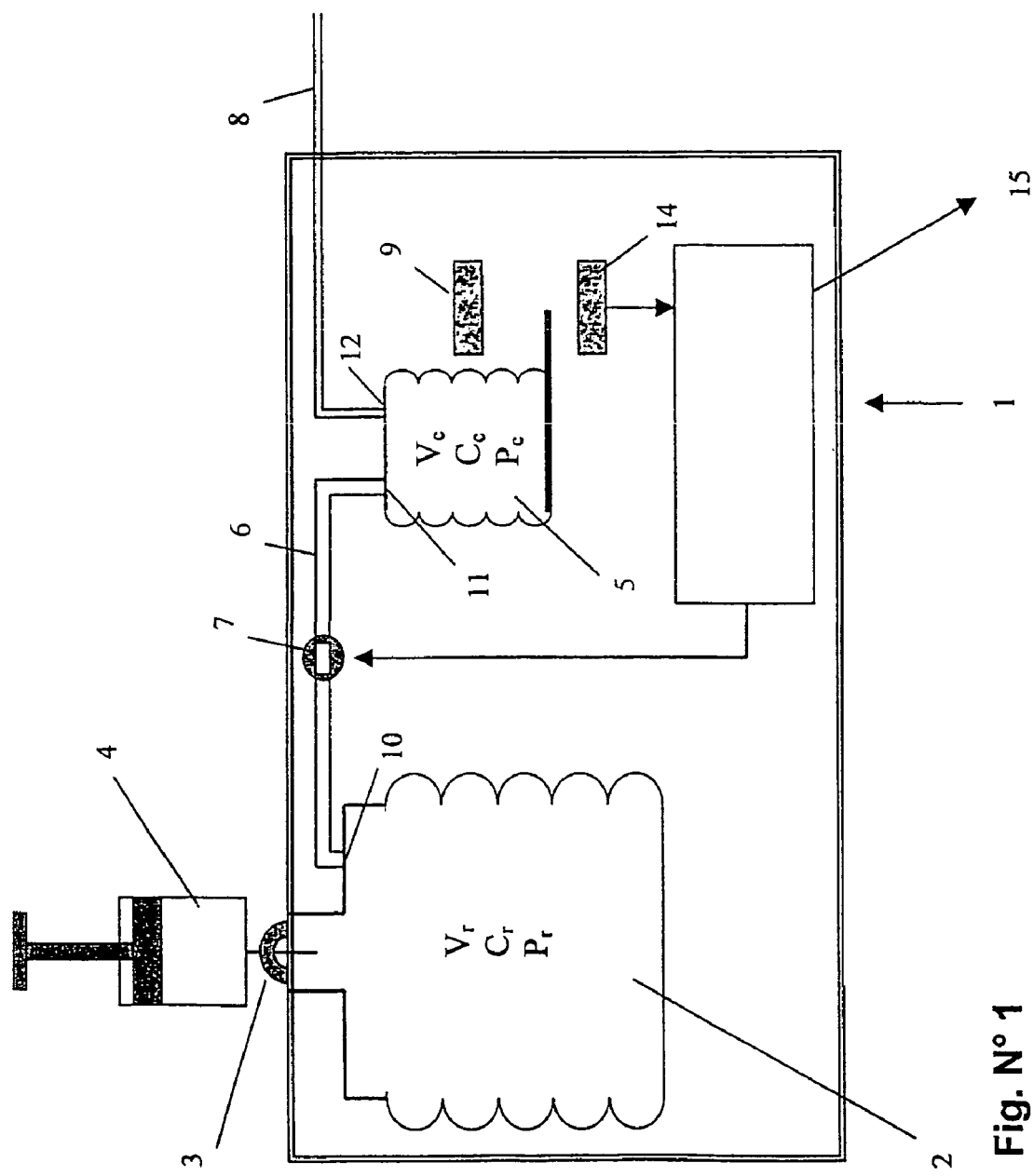
Fig. N° 1

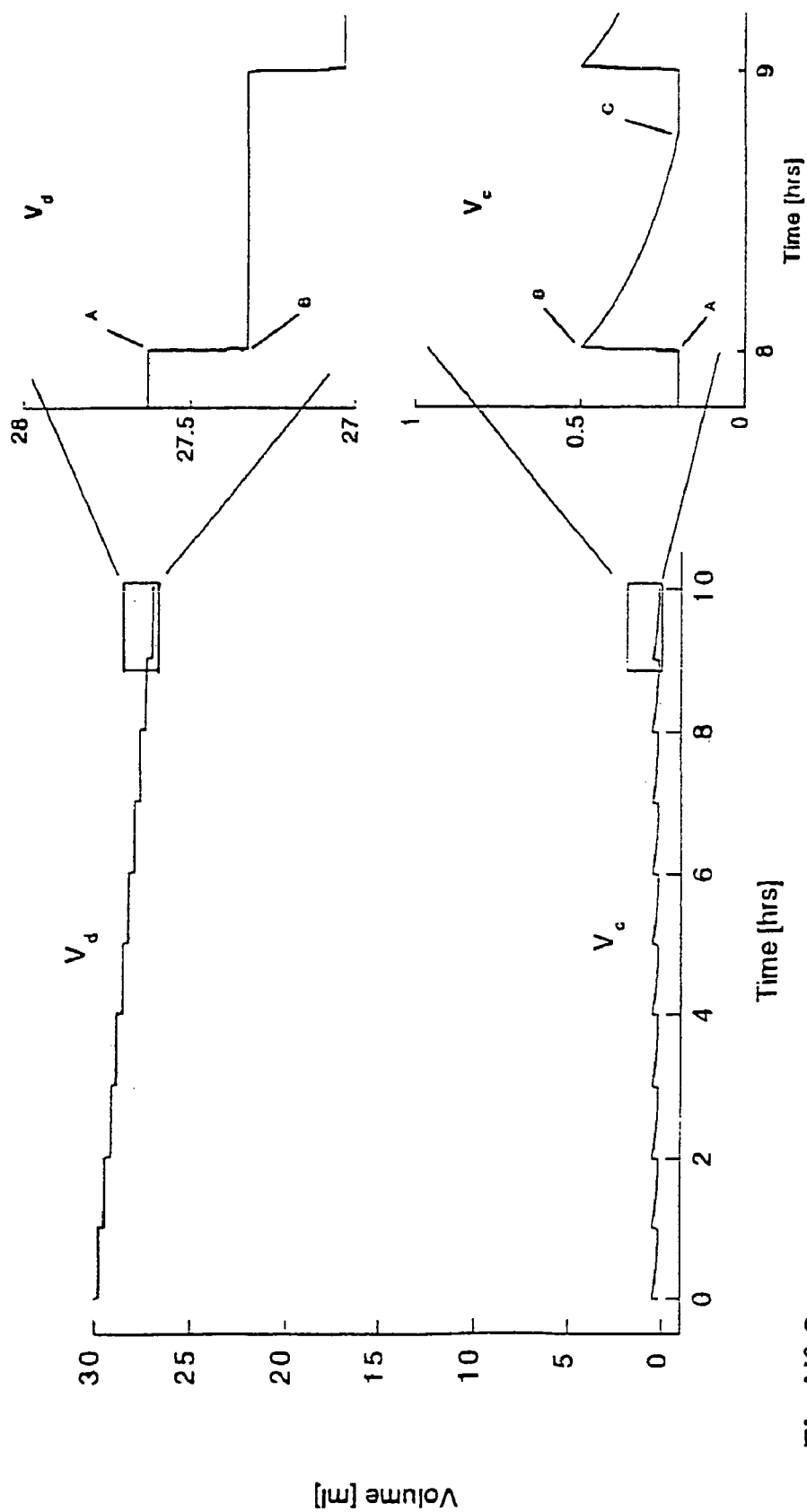
Fig N° 2

IMPLANTABLE MEDICAL DEVICE FOR DELIVERING A LIQUID

This application is the US national phase of international application PCT/CH01/00624 filed 19 Oct. 2001 which designated the U.S.

The present invention relates to an implantable medical device for administering medicines in liquid form.

The prior art includes several types of implantable devices designed for administering medicines in liquid form. The following patent documents may be cited by way of example: EP-A-409511, U.S. Pat. No. 4,673,391, WO 87/04629, WO 99/56803, U.S. Pat. No. 5,088,983, EP-B-532561, EP-A-420620 and U.S. Pat. No. 4,299,220.

These devices in most cases comprise a reservoir intended to contain the liquid before the latter is conveyed to the treatment site by way of a conduit, for example a catheter. With a number of devices, and in particular with those described in U.S. Pat. No. 5,088,983, WO 87/04629 and U.S. Pat. No. 4,299,220, the reservoir is elastic, which fact, under certain pressure conditions existing inside and/or outside the reservoir, permits passive expulsion of the liquid contained inside the reservoir.

In order to improve the control of the flowrate of the liquid expelled under such conditions, various flow regulators have been developed.

The device described in U.S. Pat. No. 4,299,220 is characterized by a flowrate regulator which comprises a variable-volume chamber formed by a membrane serving as a valve, and a conduit connecting the reservoir to the variable-volume chamber, the conduit comprising one or more flowrate limiters whose length is chosen as a function of the flowrate which it is desired to establish. In accordance with the predefined pressure conditions in the variable-volume chamber, the valve formed by the membrane permits or prevents the passage of liquid in the direction of the site to be treated.

With the devices of the prior art, such as those described above, it is always necessary, for the purpose of defining the quantity of medicine to be administered, to employ a valve or a similar system which is placed downstream of the flowrate regulator. The precision of the volume of medicine to be administered thus depends principally on the precision of the control of the valve or similar system. However, perfect control cannot be guaranteed with the devices of the prior art, and the uncertainty which exists in this regard means that the volume of medicine to be administered cannot be fixed with satisfactory precision. This problem is particularly important for treatments which demand administration of a very precise volume of medicine.

The present invention aims, among other things, to remedy this shortcoming by making available a device with improved control of the volume of liquid to be administered to the site to be treated. It relates to an implantable device for administering medicines in liquid form, comprising:
- a reservoir provided with an inlet and an outlet, said reservoir being adapted to expel the liquid,
- a variable-volume chamber provided with an inlet and an outlet, the volume of the variable-volume chamber being notably smaller than that of the reservoir,
- a first conduit connecting the outlet of the reservoir to the inlet of the variable-volume chamber in order to fill the latter,
- a second conduit, one of whose ends is connected to the outlet of the variable-volume chamber.

The originality of the invention lies principally in the fact that:
- said first conduit comprises means for interrupting and opening the flow of the liquid,
- said variable-volume chamber is adapted to expel a predefined volume $V_{exp}$ of liquid from the moment when its expansion has reached a specified value.

As will become clear from what is described below, in the context of the present invention, in contrast to the devices of the prior art, the determination of the volume to be administered is not dependent on a valve or similar means placed downstream of the variable-volume chamber.

The device according to the present invention differs from the devices of the prior art particularly by the fact that the administration of the medicament takes place in a succession of small volumes $V_{exp}$. The expression "small volume" is to be understood as a volume much smaller than that of the reservoir, preferably at least 5 times smaller.

According to another embodiment of the invention, the movement of the variable-volume chamber is kept between two values $V_{inf}$ and $V_{sup}$ by means of limiters. In such a configuration, the volume expelled $V_{exp}$ is thus equal to $V_{sup} - V_{inf}$.

In another embodiment, the position of the limiters can be varied, making it possible, with one and the same device, to choose the volume expelled $V_{exp}$ which is best suited for the treatment.

The invention will be described below with reference to the appended figures, where:

FIG. 1 shows an embodiment of the device according to the invention,

FIG. 2 is a graph showing the flowrate of the liquid as a function of time.

The implantable device (1) illustrated in FIG. 1 comprises a bellows-shaped elastic reservoir (2) intended to receive the medicine in liquid form which is introduced through an inlet (3). The latter can be formed by a septum, the medicine in this case being introduced using a syringe (4) whose needle pierces the septum.

The reservoir is connected to a variable-volume chamber (5) by way of a conduit (6) provided with a valve (7). The variable-volume chamber (5), whose volume is considerably smaller than that of the reservoir (2), is also bellows-shaped. A second conduit (8) is connected via one of its ends to the outlet (12) of the variable-volume chamber, the other end of the second conduit (8) leading to the site to be treated.

Two limiters (9, 14) are placed in such a way as to limit the variation in volume of the variable-volume chamber (5) between a smaller volume $V_{inf}$ by virtue of the lower limiter (9), and a greater volume $V_{sup}$ by virtue of the upper limiter (14).

The valve (7) placed on the first conduit (6) can be activated in different ways. It preferably has to close when the expansion of the variable-volume chamber (5) has reached a specified value. This activation can be effected electronically or mechanically. To this end, it is possible for example to provide a sensor which is situated on the surface of the limiter (14) and sends a signal to a control box (15) which then triggers the mechanism for closing the valve (7) when the variable-volume chamber has reached a certain volume called the greater volume $V_{sup}$. The control box (15) can also have a telemetry function for receiving telemetry signals (by radio frequency or otherwise) which are sent from outside and which serve to transmit the parameters for the control and functioning of the apparatus. These parameters are, for example, the period of the opening/closing cycle of the valve (7) and the position of the limiters (9, 14).

The principle by which the device described in FIG. 1 functions is as follows:

In a first step, the elastic reservoir (2) is filled by means of a syringe (4), the valve (7) being closed. Starting from a certain degree of extension of the elastic reservoir (2), the restoring force of the latter is such that the liquid can be expelled into the conduit (6).

When the valve (7) is open, the liquid is conveyed toward the variable-volume chamber (5). As soon as the greater volume $V_{sup}$ of the variable-volume chamber is reached, the valve (7) closes and the liquid is conveyed by the restoring force of the variable-volume chamber (5) into the second conduit (8) and toward the site to be treated.

When the variable-volume chamber (5) is at its smaller volume level $V_{inf}$, liquid is no longer expelled from it. At the end of a time interval Δt, determined as a function of the desired dosage, the valve (7) opens again and the process described above is repeated. The medicine is thus administered in a succession of expulsions of doses whose volume $V_{exp}=V_{sup}-V_{inf}$ is known with precision. The result of this is that the total quantity of medicine to be administered can be determined very precisely by virtue of the device of the invention.

FIG. 2 shows a graph illustrating the functioning of the apparatus. The left-hand part of the graph shows the variation of the volume of the elastic reservoir (2) $V_d$ and that of the volume of the variable-volume chamber (5) $V_c$ during 10 operating cycles of the apparatus. In this example, the period of each cycle is one hour, the initial volume of the elastic reservoir (2) $V_d$ is 30 ml and drops to 5 ml once all the liquid is expelled, and the greater volume $V_{sup}$ and smaller volume $V_{inf}$ of the variable-volume chamber (5) are respectively 0.5 ml and 0.2 ml. The volume expelled $V_{exp}$ from the variable-volume chamber in each operating cycle is thus 0.3 ml, which gives a mean flowrate of expelled liquid of $V_{exp}/T$, or 0.3 ml/hour. The compliance of the elastic reservoir (2) is 0.1 ml/mmHg while that of the variable-volume chamber (5) is 0.02 ml/mmHg. The resistance at the inlet of the variable-volume chamber (5) is 20,000 mmHg/(ml/s) while the outlet resistance rises to 100,000 mmHg/(ml/s).

In short, the parameters must be chosen so that the pressure is always higher in the elastic reservoir (2) than it is in the variable-volume chamber (5), this in order to ensure filling and sufficient pressure of the variable-volume chamber (5) in order to allow the liquid to be expelled from it.

The right-hand part of FIG. 2 shows two enlargements of its left-hand part, i.e. the variation in the volumes $V_d$ and $V_c$ during 1 operating cycle. The points A and B correspond to the moment of opening and closure of the valve (7). The point C corresponds to the moment when the expulsion of the liquid from the variable-volume chamber (5) is interrupted by the limiter (9).

It should be noted that, during the filling of the variable-volume chamber (5), a minuscule quantity of liquid may pass directly into the second conduit (8) so that at each cycle, in addition to the volume expelled $V_{exp}$, a supplementary volume is administered. This supplementary volume is minimal if the phase of filling of the variable-volume chamber (5) is very short in relation to the phase of expulsion of the liquid (that is to say the time between points A and B is much less than the time between points B and C). In some cases, it may be useful to minimize this supplementary volume, or eliminate it altogether, in order to determine as precisely as possible the quantity of medicine to be administered. This can be done by using a second conduit (8) whose resistance to the flow of the liquid is notably greater than that of the first conduit (6). Alternatively, or in addition to this, it is possible to place a valve of the ON/OFF type on the second conduit (8), the latter closing when the valve (7) of the first conduit (6) opens.

It should be emphasized that a volume expelled $V_{exp}$ toward the site to be treated is known with a very high degree of precision. This is because it is determined by a statistical method, namely measurement of the difference between the greater volume $V_{sup}$ and the smaller volume $V_{inf}$, these two volumes being known indirectly by the position of the limiters (9, 14).

If the device does not include limiters, the volume expelled can be determined at the place of production.

Besides the fact that $V_{exp}$ can be determined very precisely, the value Δt is determined with a high degree of precision. It then becomes possible to predict the exact quantity of medicine which is actually administered and the mean flowrate of administration. Conversely, in the devices of the prior art, the expelled volume is determined by dynamic measurement, that is to say as a function of the flowrate and the time of opening of the valve. The knowledge of the volume expelled can only be more imprecise in this case.

In principle, the mean flowrate of the liquid expelled is equal to $V_{exp}/T$, this value itself being equal to the variation in volume of the reservoir (2) $V_d$ in relation to the time. It is thus possible to use a sensor which measures with great precision the volume $V_d$ in order to permanently permit control of the mean flowrate.

It should be noted that the invention is not limited to elastic reservoirs which expel liquid in a passive manner. It is perfectly conceivable to design a system in which the reservoir is placed in a cavity filled with a gas and the increase in the pressure of the gas in the cavity reduces the volume of the reservoir in order to expel the liquid. Nor is it necessary to employ an elastic reservoir; any implantable reservoir provided with a system for expulsion of the liquid can be considered.

Likewise, the variable-volume chamber does not have to be bellows-shaped. For example, it is possible to use a balloon whose compliance is high during filling and almost zero when filled.

Finally, it should be noted that the number of elastic reservoirs used with the device according to the present invention is not limited. It is perfectly conceivable to use at least two reservoirs, each one containing a different medicine, each reservoir opening in succession and/or alternately or simultaneously if the two medicines are to be mixed prior to their administration.

With such a design, a single multiple valve can be used, each elastic reservoir being connected to said multiple valve.

What is claimed is:

1. An implantable device (1) for administering medicines in liquid form, comprising:
   a reservoir (2); a variable-volume chamber (5) having a volume determined by a position of at least a first movable volume limiter;
   a first conduit (8) connecting the reservoir (2) to the variable-volume chamber (5) in order to fill the latter, said first conduit (8) comprising a valve;
   a second conduit (8) coupled to the variable-volume chamber (5), the second conduit having an outlet end adapted to be disposed at a treatment site; and
   a control box coupled to the valve and the at least first volume limiter, the control box programmed to control actuation of the valve and positioning of the first movable volume limiter.

2. The device of claim 1 wherein the valve is activated when the variable-volume chamber (5) attains a predetermined volume.

3. The device of claim 1, wherein the control box is programmed to actuate the valve at regular time intervals $\Delta t$.

4. The device of claim 1, wherein the resistance to the flow of the fluid in the second conduit (8) is greater than that of the first conduit (6).

5. The device of claim 1, wherein the control box is configured to receive control parameters telemetrically.

6. The device of claim 1, wherein a volume of the reservoir (2) is at least 5 times greater than that of the variable-volume chamber (5).

7. The device of claim 1, further comprising a second movable volume limiter.

8. The device of claim 7, wherein the control box further is programmed to control a position of the second movable volume limiter.

9. The device of claim 1 wherein the reservoir is elastically deformable.

10. The device of claim 7 wherein the second movable volume limiter further comprises a sensor, the sensor generating a signal that triggers expulsion of medicine from the variable-volume chamber.

11. An implantable pump for delivery of a drug, the implantable pump comprising:
    a reservoir that deforms elastically when it is filled with the drug;
    a chamber having a volume determined by a position of a first movable volume limiter;
    a valve interposed between the reservoir and the chamber, the valve configured to be electrically activated;
    an outlet catheter in fluid communication with the chamber; and
    a control box programmed to control actuation of the valve and positioning of the first movable volume limiter.

12. The pump of claim 11 wherein the control box is configured to receive control parameters telemetrically.

13. The pump of claim 11 wherein the reservoir further comprises a resealable septum.

14. The pump of claim 11 wherein the valve is activated when the variable-volume chamber attains a predetermined volume.

15. The pump of claim 11 wherein the control box is programmed to actuate the valve at regular time intervals $\Delta t$.

16. The pump of claim 11, wherein a volume of the reservoir is at least 5 times greater than that of the chamber.

17. The pump of claim 11 wherein the chamber is elastically deformable.

18. The pump of claim 11, further comprising a second movable volume limiter.

19. The pump of claim 18 wherein the control box further is programmed to control a position of the second movable volume limiter.

20. The pump of claim 11 further comprising a sensor that triggers expulsion of medicine from the chamber.

* * * * *